United States Patent
Cleugh

(10) Patent No.: US 7,268,249 B2
(45) Date of Patent: Sep. 11, 2007

(54) PRODUCTION PROCESS OF OPTICALLY PURE 2-(4-HYDROXYPHENOXY)-PROPIONIC ACID COMPOUNDS

(75) Inventor: Ernest Stephen Cleugh, West Yorkshire (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 10/571,863

(22) PCT Filed: Aug. 16, 2004

(86) PCT No.: PCT/GB2004/003497

§ 371 (c)(1),
(2), (4) Date: Mar. 14, 2006

(87) PCT Pub. No.: WO2005/042460

PCT Pub. Date: May 12, 2005

(65) Prior Publication Data

US 2006/0270851 A1   Nov. 30, 2006

(30) Foreign Application Priority Data

Sep. 30, 2003   (GB) .................. 0322917.6

(51) Int. Cl.
*C07C 69/76* (2006.01)
*C07C 59/00* (2006.01)
(52) U.S. Cl. ....................... 560/61; 562/471
(58) Field of Classification Search .......... 560/61; 562/471
See application file for complete search history.

(56) References Cited

U.S. PATENT DOCUMENTS 4,532,346 A   7/1985   Rehn et al.
4,625,053 A   11/1986   Fujinawa et al.

*Primary Examiner*—Thurman K. Page
*Assistant Examiner*—Lalitha Nagubandi
(74) *Attorney, Agent, or Firm*—William A. Teoli, Jr.

(57) ABSTRACT

A process for producing optically pure R-hydroxyphenoxypropanoic acid or a salt or ester thereof by reaction of hydroquinone or a salt thereof with an S-halopropanoic acid or a salt thereof in the presence of a mild reducing agent.

8 Claims, No Drawings

PRODUCTION PROCESS OF OPTICALLY PURE 2-(4-HYDROXYPHENOXY)-PROPIONIC ACID COMPOUNDS

This application is a 371 of International Application No. PCT/GB2004/003497 filed Aug. 16, 2004, which claims priority to GB 0322917.6 filed Sep. 30, 2003, the contents of which are incorporated herein by reference.

The present invention relates to a process for the production of optically pure R-hydroxyphenoxypropanoic acid or a salt or ester thereof and its use in making herbicidal products on an industrial scale.

Optically pure R-2-(4-hydroxyphenoxy)propanoic acid (3) can be prepared by the reaction of hydroquinone (2) with an S-2-halopropanoic acid (1) where X is chloro or bromo and is preferably chloro, in the presence of a base.

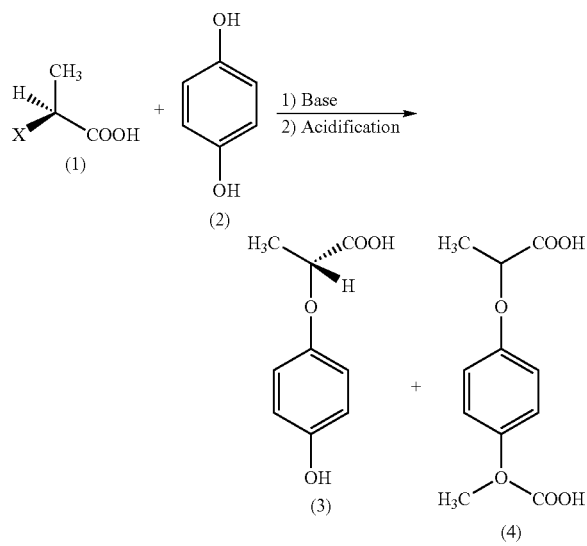

The problems associated with producing optically pure R-2-(4-hydroxyphenoxy)propanoic acid from hydroquinone and an S-2-halopropanoic acid are discussed and the relevant prior art is reviewed in EP352168. In particular, over-alkylation of hydroquinone to give the bis-acid (4) and oxidation of hydroquinone to give highly coloured by-products are two serious problems. The solution offered in EP352168 is to perform a complex purification procedure.

On an industrial scale it is desirable to have a simple method for the preparation of R-2-(4-hydroxyphenoxy)propanoic that is essentially free of products of over-alkylation, that is not contaminated by highly coloured by-products and therefore does not require any complex or expensive purification procedures. The applicants have surprisingly found that the use of a mild reducing agent in the manufacture of R-2-(4-hydroxyphenoxy)propanoic acid enables a product to be isolated that meets the above criteria.

There is therefore provided a process for producing R-2-(4-hydroxyphenoxy)propanoic acid by reaction of hydroquinone or a salt thereof with an S-2-halopropanoic acid or a salt thereof, in the presence of a mild reducing agent.

The S-2-halopropanoic acid is S-2-bromopropanoic acid or S-2-chloropropanoic acid, preferably S-2-chloropropanoic acid.

In one preferred embodiment excess hydroquinone is recovered for recycle.

It is preferred that isolation of the R-2-(4-hydroxyphenoxy)propanoic acid produced by the reaction is carried out by acidification for example with a mineral acid, especially hydrochloric acid, and filtration.

If necessary or desired the R-2-(4-hydroxyphenoxy)propanoic acid may be converted to a salt or ester thereof by conventional techniques.

The preferred solvents for the reaction are water or water miscible solvents such as methanol or ethanol, alone or in admixture with water.

Preferred bases are alkali metal hydroxides especially sodium hydroxide.

Preferably the reaction is carried out at a temperature of 10-100° C., more preferably 30-70° C.

The reaction may be carried out at atmospheric pressure or up to 1 bar of excess pressure.

It is advantageous to use a deficiency of the S-2-halopropanoic acid, as its salt, in the reaction with hydroquinone, typically 0.25-0.75 mol/mol and preferably 0.3-0.6 mol/mol. Preferred salts are alkali metal salts, more preferably the sodium salt.

Suitably an excess of a stoichiometric amount of base on the hydroquinone is used. Preferably the base is used at between 1.5 and 2.5 mol/mol on hydroquinone and more preferably at 1.6-2.0 mol/mol.

The mild reducing agent is preferably present throughout the process. It may be added to the process as a solid or as a solution. Incremental additions may be made during the process.

Suitably the mild reducing agent is a neutral or a charged low oxidation state sulphur species, such as sulphur dioxide, a sulphite, a bisulphite, a hydrosulphite, a metabisulphite, a sulphenic acid, a sulphinic acid, for example formamidine sulphinic acid, or a low oxidation state phosphorous species such as a phosphite or hypophosphite, or hydrazine, a hydrazine derivative, or ascorbic acid.

Preferred mild reducing agents are alkali metal sulphite or bisulphite salts such as sodium sulphite, sodium bisulphite, potassium sulphite or potassium bisulphite.

A preferred mild reducing agent is sodium bisulphite.

The amount of the mild reducing agent used is between 0.01% and 10% by weight on the amount of hydroquinone and is preferably between 0.1% and 5% and most preferably between 0.5% and 2%.

The process is preferably conducted essentially in the absence of oxygen by use of an inert gas blanket, for example nitrogen.

If desired the process can be adopted for the production of S-2-(4-hydroxyphenoxy)propanoic acid by substituting an R-2-halopropanoic acid for the S-2-halopropanoic acid as a starting material.

R-2-(4-hydroxyphenoxy)propanoic acid is used in the manufacture of several commercial herbicides such as quizalofop-P-ethyl, haloxyfop-P-methyl, fluazifop-P-butyl, clodinafop, cyhalofop-butyl and fenoxaprop-P-ethyl.

Therefore, in another aspect of the invention there is provided a process for the manufacture of quizalofop-P-ethyl, haloxyfop-P-methyl, fluazifop-P-butyl, clodinafop, cyhalofop-butyl or fenoxaprop-P-ethyl by a) producing R-2-(4-hydroxyphenoxy)propanoic acid by reaction of hydroquinone or a salt thereof with a S-2-halopropanoic acid or a salt thereof, in the presence of a mild reducing agent, b) reacting the R-2-(4-hydroxyphenoxy)propanoic acid with the appropriate halo-aryl or halo-heteroaryl moiety to give a R-2-((4-aryloxy or heteroaryloxy)phenoxy)propanoic acid and c) esterification of the acid from step b) to give quizalofop-P-ethyl, haloxyfop-P-methyl, fluazifop-P-butyl, clodinafop, cyhalofop-butyl or fenoxaprop-P-ethyl.

The appropriate halo-aryl or halo-heteroaryl moieties are 2-halo-6-chloro-quinoxaline for quizalofop-P-ethyl; 2-halo-3-chloro-5-trifluoromethylpyridine for haloxyfop-P-methyl; 2-halo-5-trifluoromethylpyridine for fluazifop-P-butyl; 2-halo-5-chloro-3-fluoropyridine for clodinafop; 4-halo-3-fluorobenzonitrile for cyhalofop-butyl and 2-halo-6-chloro-benzoxazole for fenoxaprop-P-ethyl where halo is chloro or bromo.

The conversion of R-2-(4-hydroxyphenoxy)propanoic acid to the acids of step b) and and esters of step c) is well known to the skilled person e.g. in Advanced Organic Chemistry, Jerry March, John Wiley & Sons, 1992, p 393.

The invention will now be further illustrated with reference to the following Example.

The product quality was determined by HPLC and the colour was determined as follows. About 10 gm of R-2-(4-hydroxyphenoxy)propanoic acid was suspended in 10 mls water and adjusted to pH 7 with potassium hydroxide solution before being made up to 10 mls with more water. The absorbances of the solution were measured at 420 and 650 nm and are expressed as extinctions coefficients ($\epsilon$, absorbance for a 1 molar solution and a 1 cm path length.).

EXAMPLE 1

Preparation of R-2-(4-hydroxyphenoxy)propanoic acid in the presence of sodium bisulphite with recycling of hydroquinone Step 1

Hydroquinone (574 g, 5.22 mol) was charged to a reaction flask followed by sodium bisulphite (5.74 g) and water (1014 g) and a nitrogen blanket was established. The mixture was stirred and heated to 50° C. and 47% solution of sodium hydroxide (799.5 g, 9.39 mol) was added. The solution was heated to 65° C. and an aqueous solution of S-2-chloropropanoic acid sodium salt (544.4 g, 32.5% as the free acid, 1.63 mol) was added. The reaction mixture was held at 65° C. for 4 hours. After this period, the total reaction mass weighed 2937.6 g and had a R-2-(4-hydroxyphenoxy)propanoic acid content of 8.60%, equivalent to 252.54 product or 85% yield. 700 g of water were added and the temperature adjusted to below 45° C. Phosphoric acid (120 g) was added to adjust the pH to about 11 and then 98% sulphuric acid (250 g) was added to reduce the pH to 6.5-7.5, the temperature being controlled at 55° C. during these additions. The solution was then extracted with four successive 638 ml portions of methylisobutylketone (MiBK) to give a solution of hydroquinone in MiBK for use in the next cycle.

Step 2.

The MiBK extracts of hydroquinone were then extracted with a solution of sodium hydroxide (687 g 47% solution), sodium bisulphite (4.02 g) and water (1013 g) whilst maintaining an inert atmosphere (nitrogen). The aqueous extract of hydroquinone was charged to a reaction flask followed by fresh hydroquinone (172.2 g), 47% sodium hydroxide solution (111.9 g) and sodium bisulphite (1.72 g), all under a nitrogen blanket. The solution was heated to 65° C. and an aqueous solution of S-2-chloropropanoic acid sodium salt (544.4 g, 32.5% as the free acid, 1.63 mol) was added at this temperature. The reaction mixture was held at 65° C. for 4 hours. 700 g of water were added and the temperature adjusted to below 45° C. Phosphoric acid (120 g) was added to adjust the pH to about 11 and then 98% sulphuric acid (250 g) was added to reduce the pH to 6.5-7.5, the temperature being controlled at 55° C. during these additions.

The un-reacted hydroquinone was removed by extraction with MiBK as above and the residual aqueous phase was then adjusted to pH 2±0.2 using 98% sulphuric acid and extracted with two 250 ml portions of MiBK to extract the R-2-(4-hydroxyphenoxy)propanoic acid. The two extracts were combined and washed with a solution of potassium hydroxide (155.5 g of 85% strength material) and sodium bisulphite (2.15 g) in water (280 g).

The aqueous solution of R-2-(4-hydroxyphenoxy)propanoic acid potassium salt was acidified to pH 1 with 32% hydrochloric acid and the temperature adjusted to 20° C. The slurry was then filtered and the solid product washed with water (one wash 260 g and then two washes at 230 g). After washing, the product was dried before weighing and analysis.

Weight 188 g
Strength 99.4%
Bis acid 0.3%
Yield 63%
Colour Absorbance at 650 nm, 0.023, at 420 nm, 0.197

The table below gives absorbance data for product obtained by the process of the invention and the same process but without the use of sodium bisulphate.

| Reaction | Observed color | $\epsilon$ at 650 nm | $\epsilon$ at 420 nm |
| --- | --- | --- | --- |
| Control without any sodium bisulphite | Light brown | 0.153 | 1.614 |
| Addition of 5% sodium bisulphite on hydroquinone | White | 0.061 | 0.243 |

The invention claimed is:

1. A process for producing R-2-(4-hydroxyphenoxy)propanoic acid or a salt thereof by reaction of hydroquinone or a salt thereof with a S-2-halopropanoic acid or a salt thereof in the presence of a mild reducing agent.

2. A process according to claim 1 wherein the S-2-halopropanoic acid is S-2-chloropropanoic acid.

3. A process according to claim 1 wherein the excess hydroquinone is recovered for recycle.

4. A process according to claim 1 wherein the mild reducing agent is a neutral or a charged low oxidation state sulphur species, a low oxidation state phosphorous species, hydrazine, a hydrazine derivative or ascorbic acid.

5. A process according to claim 4 wherein the mild reducing agent is sulphur dioxide, a sulphite, a bisulphite, a hydrosulphite, a metabisulphite, a sulphenic acid, a sulphinic acid, a phosphite, hypophosphite, hydrazine, a hydrazine derivative or ascorbic acid.

6. A process according to claim 5 wherein the mild reducing agent is an alkali metal sulphite or bisulphite.

7. A process for the manufacture of quizalofop-P-ethyl, haloxyfop-P-methyl, fluazifop-P-butyl, clodinafop, cyhalofop-butyl or fenoxaprop-P-ethyl by:
   a) producing R-2-(4-hydroxyphenoxy)propanoic acid by reaction of hydroquinone or a salt thereof with S-2-halopropanoic acid or a salt thereof, in the presence of a mild reducing agent,
   b) reacting the R-2-(4-hydroxyphenoxy)propanoic acid with the appropriate halo-aryl or halo-heteroaryl moiety to give a R-2-((4-aryloxy or heteroaryloxy)phenoxy)propanoic acid and
   c) esterification of the acid from step b) to give quizalofop-P-ethyl, haloxyfop-P-methyl, fluazifop-P-butyl, clodinafop, cyhalofop-butyl or fenoxaprop-P-ethyl.

8. A process according to claim 5 wherein the sulphinic acid is formamidine sulphinic acid.

* * * * *